US012794189B2

(12) United States Patent
Umemura et al.

(10) Patent No.: US 12,794,189 B2
(45) Date of Patent: Nov. 10, 2026

(54) 215- TO 222-NM WAVELENGTH LASER LIGHT GENERATING DEVICE

(71) Applicants: Nobuhiro Umemura, Chitose (JP); JOSHO GAKUEN EDUCATIONAL FOUNDATION, Osaka (JP); TOSOH SGM CORPORATION, Shunan (JP)

(72) Inventors: Nobuhiro Umemura, Hokkaido (JP); Tomosumi Kamimura, Osaka (JP); Hideharu Horikoshi, Yamaguchi (JP)

(73) Assignees: Nobuhiro Umemura, Hokkaido (JP); JOSHO GAKUEN EDUCATIONAL FOUNDATION, Osaka (JP); TOSOH SGM CORPORATION, Yamaguchi (JP)

(*) Notice: Subject to any disclaimer, the term of this patent is extended or adjusted under 35 U.S.C. 154(b) by 597 days.

(21) Appl. No.: 18/547,604

(22) PCT Filed: Feb. 24, 2022

(86) PCT No.: PCT/JP2022/007566
§ 371 (c)(1),
(2) Date: Aug. 23, 2023

(87) PCT Pub. No.: WO2022/181676
PCT Pub. Date: Sep. 1, 2022

(65) Prior Publication Data

US 2024/0131208 A1 Apr. 25, 2024
US 2024/0226347 A9 Jul. 11, 2024

(30) Foreign Application Priority Data

Feb. 24, 2021 (JP) ................................. 2021-027496

(51) Int. Cl.
*H01S 3/00* (2006.01)
*A61L 2/10* (2006.01)
(Continued)

(52) U.S. Cl.
CPC .............. *H01S 3/0092* (2013.01); *A61L 2/10* (2013.01); *G02F 1/354* (2021.01); *G02F 1/37* (2013.01);
(Continued)

(58) Field of Classification Search
CPC ...... H01S 3/0092; H01S 3/00; H01S 3/08004; H01S 3/1083; H01S 3/109; H01S 3/1643;
(Continued)

(56) References Cited

U.S. PATENT DOCUMENTS 6,249,371 B1 6/2001 Masuda et al.
6,373,869 B1 * 4/2002 Jacob .................... G02F 1/3534 372/5

(Continued)

FOREIGN PATENT DOCUMENTS

CN 111404011 7/2020
CN 112003118 11/2020

(Continued)

OTHER PUBLICATIONS

Sakuma, et al., "Generation of all-solid-state, high-power continuous-wave 213-nm light based on sum-frequency mixing in CsLiB6O10", Optics Letters, vol. 29, No. 10, May 15, 2004, pp. 1096-1098.

(Continued)

*Primary Examiner* — Yuanda Zhang
(74) *Attorney, Agent, or Firm* — HSML P.C.

(57) ABSTRACT

The present invention relates to a 215- to 222-nm wavelength laser light generating device comprising: an excitation light source part for converting a laser light with a wavelength of 1030 to 1064 nm to a second harmonic, and generating a laser light with a wavelength of 515 to 532 nm; an optical parametric oscillating part for generating a signal light with a wavelength of 858 to 887 nm and an idler light with a wavelength of 1288 to 1330 nm using the laser light
(Continued)

with the wavelength of 515 to 532 nm as an excitation light; a separating part for separating the signal light and the idler light; a first wavelength converting part for generating a fourth harmonic from the signal light; a second wavelength converting part for generating a deep ultraviolet light with a wavelength of 215 to 222 nm by sum frequency with a second harmonic of the excitation light from the idler light; and a coupling part for coupling the fourth harmonic from the first wavelength converting part and the deep ultraviolet light from the second wavelength converting part. The present invention provides a laser generating device that enables to generate simply and efficiently a pulse laser light with a wavelength of 215 to 222 nm including a wavelength of 222 nm disinfecting microorganisms.

10 Claims, 4 Drawing Sheets

(51) Int. Cl.

| | |
|---|---|
| ***G02F 1/35*** | (2006.01) |
| ***G02F 1/37*** | (2006.01) |
| ***G02F 1/39*** | (2006.01) |
| ***H01S 3/08*** | (2023.01) |
| ***H01S 3/108*** | (2006.01) |
| ***H01S 3/109*** | (2006.01) |
| ***H01S 3/16*** | (2006.01) |
| ***H01S 5/00*** | (2006.01) |
| *A61L 103/05* | (2026.01) |

(52) U.S. Cl.

CPC ................ *G02F 1/39* (2013.01); *G02F 1/392* (2021.01); *H01S 3/00* (2013.01); *H01S 3/08004* (2013.01); *H01S 3/1083* (2013.01); *H01S 3/109* (2013.01); *H01S 3/1643* (2013.01); *H01S 5/0071* (2013.01); *A61L 2103/05* (2026.01); *A61L 2202/11* (2013.01)

(58) Field of Classification Search

CPC .......... H01S 5/0071; A61L 2/10; G02F 1/354; G02F 1/37; G02F 1/39; G02F 1/392

See application file for complete search history.

(56) References Cited

U.S. PATENT DOCUMENTS

| | | | | |
|---|---|---|---|---|
| 6,477,188 | B1 | 11/2002 | Takaoka et al. | |
| 2002/0095142 | A1 * | 7/2002 | Ming | A61F 9/008 606/5 |
| 2007/0064749 | A1 | 3/2007 | Kaneda et al. | |
| 2012/0026578 | A1 | 2/2012 | Sakuma | |
| 2013/0313440 | A1 | 11/2013 | Chuang et al. | |
| 2016/0099540 | A1 * | 4/2016 | Chuang | H01S 3/10084 372/5 |
| 2016/0116822 | A1 | 4/2016 | Kaneda | |

FOREIGN PATENT DOCUMENTS

| | | |
|---|---|---|
| JP | 2003-005233 | 1/2003 |
| JP | 2003-280055 | 10/2003 |
| JP | 2007-086101 | 4/2007 |
| JP | 2012-252289 | 12/2012 |
| JP | 2016-220684 | 12/2016 |
| JP | 2017-136145 | 8/2017 |
| JP | 2018-114197 | 7/2018 |
| KR | 20150016584 A | 2/2015 |
| TW | 201349688 | 12/2013 |
| TW | 201830809 | 8/2018 |
| WO | 99/14631 | 3/1999 |
| WO | 2012/122210 | 9/2012 |
| WO | 2013/177000 | 11/2013 |
| WO | 2013177000 A1 | 11/2013 |
| WO | 2015/174388 | 11/2015 |
| WO | 2018/128963 | 7/2018 |

OTHER PUBLICATIONS

Mirov, et al., "All-solid-state laser system tunable in deep ultraviolet based on sum-frequency generation in CLBO", Optics Communications vol. 198, Nov. 1, 2001, pp. 403-406.

International Search Report issued in International Application No. PCT/JP2022/007566, May 10, 2022, 12 pages w/ translation.

International Preliminary Report on Patentability issued in International Application No. PCT/JP2022/007566, Sep. 7, 2023, 6 pages w/ translation.

Petrov, et al., "Frequency Conversion of Ti:Sapphire-Based Femtosecond Laser Systems to the 200-nm Spectral Region Using Nonlinear Optical Crystals", IEEE Journal of Selected Topics in Quantum Electronics, vol. 5, No. 6, Dec. 1, 1999, pp. 1532-1542.

Extended European Search Report issued in corresponding European Patent Application No. 22759711.9, Feb. 28, 2025, 14 pages.

Office Action dated Aug. 27, 2024 issued in the corresponding Korean patent application No. 10-2023-7032353 with its English Machine Translation, 16 pages.

* cited by examiner

215- TO 222-NM WAVELENGTH LASER LIGHT GENERATING DEVICE

TECHNICAL FIELD

The present invention relates to a 215- to 222-nm wavelength laser light generating device. More particularly, the present invention relates to an all-solid-state wavelength conversion laser generating device not affecting the human body, and for generating a laser light with a wavelength 215 to 222 nm of a deep ultraviolet laser light having a disinfecting effect (including inactivation of virus: the same shall apply hereinafter) with high efficiency.

CROSS-REFERENCE TO RELATED APPLICATIONS

The present application claims the priority of Japanese Patent Application No. 2021-027496 filed on Feb. 24, 2021, the entire contents of which is herein incorporated by reference.

BACKGROUND ART

As a means for inactivating microorganisms such as bacteria and virus, deep ultraviolet ray irradiation has been used from old times. This uses the following: in DNA which has absorbed a deep ultraviolet light, optical chemical reactions such as dimer formation and decomposition are effected, which breaks the helical structure of DNA, thereby forming cyclobutane pyrimine, resulting in extinction of the bacteria cell.

The deep ultraviolet rays conventionally used are not used for human in consideration of the effect on the human body. However, despite of the fact that a deep ultraviolet light with a wavelength of 222 nm has the disinfecting effect roughly equal to that of the disinfecting ultraviolet light conventionally used, or higher effect according to the bacterial strain, it is absorbed by the stratum corneum of the skin of the human. For this reason, the deep ultraviolet light with a wavelength of 222 nm less affects the human body as compared with conventional ultraviolet rays, and hence has attracted attention.

As a source of generation of a light with a wavelength of 222 nm, a UV lamp such as a KrCl lamp is known. However, the emission spectrum of the UV lamp also includes a deep ultraviolet light with a wavelength detrimental to the human body other than 222 nm. For this reason, a filter for cutting the lights is required to be used in combination (e.g., PTL 1, 2, and 3). For this reason, the effective disinfecting effect could not be obtained. Further, a light emitting diode (LED) noted as the alternative light source of a mercury lamp can provide only an output of microwatt order with a wavelength of 265 nm or less at present.

Generally, a laser light is narrower in spectrum than a UV lamp, and a laser light source for oscillating only a deep ultraviolet ray with a wavelength around 222 nm contributing to disinfection would be very useful. A laser light is good in directivity, and hence can be applied with the power concentrated to a narrow area. This enables much deep ultraviolet light to reach each DNA at the cell wall and in the cell membrane inside of a microorganism. Thus, the disinfecting effect in a short time can be expected. In recent years, a semiconductor laser has attracted attention as an alternative light source of a mercury lamp. However, oscillation at a high output with a wavelength of 270 nm or less has not been reported, and a laser light source for oscillating only a deep ultraviolet ray with a wavelength of around 222 nm is not known.

As the deep ultraviolet laser light source, for example, a KrF laser device is known. The oscillation wavelength is 248 nm. Alternatively, a deep ultraviolet light with a wavelength of 266 nm by the fourth harmonic generation of a Nd:YAG laser with oscillation of a wavelength of 1064 nm is known. However, the wavelength is not 222 nm. Further, the wavelengths are of deep ultraviolet rays affecting the human body.

[PTL 1] Japanese Patent Application Publication No. 2016-220684

[PTL 2] Japanese Patent Application Publication No. 2017-136145

[PTL 3] Japanese Patent Application Publication No. 2018-114197

[PTL 4] Japanese Patent Application Publication No. 2007-86101

[PTL 5] Japanese Patent Application Publication No. 2003-5233

[PTL 6] Japanese Patent Application Publication No. 2003-280055

The entire contents of PTL 1 to 6 are herein incorporated particularly as disclosure.

SUMMARY OF INVENTION

Technical Problem

For this reason, there is a need for a 222 nm wavelength laser light generating device using the existing laser light source, and capable of using a light from the light source with efficiency. Particularly, the emergence of a 222-nm wavelength laser light generating device by an all-solid-state system using a nonlinear optical element has been desired.

Although an all-solid-state laser which is compact and good in maintainability has been demanded as a deep ultraviolet light source for generating a deep ultraviolet light with a wavelength of 222 nm with efficiency, sufficient performances could not be obtained with a device using a conventional semiconductor laser or a device using an excimer laser.

For example, PTL 4 discloses a laser device for generating a laser light within the deep ultraviolet region of a wavelength of 190 to 270 nm using two semiconductor laser light sources. Although the device provides a laser light of 227 nm using a nonlinear optical element, there is no description that a laser light with a wavelength of 222 nm is generated.

A deep-ultraviolet-region laser light generating device using a semiconductor laser light source and a nonlinear optical element is disclosed in PTL 5. A deep-ultraviolet-region laser light generating device using a semiconductor laser light source, a nonlinear optical element, and an optical parametric oscillator is disclosed in PTL 6. However, for the device disclosed in PTL 5, the ultraviolet ray wavelength to be targeted is different, and is the fifth harmonic resulting from the KBBF crystal of an output light of a titanium sapphire laser with a wavelength of 788.145 nm. This is not a 222-nm wavelength laser light generating device.

The device disclosed in PTL 6 is also different in ultraviolet ray wavelength to be targeted, and is not a 222-nm wavelength laser light generating device. The device uses an output light of second harmonic excited optical parametric oscillation of a Nd:YAG laser, but does not use an idler light of optical parametric oscillation. The device is different in this point from the present invention.

The present invention was completed in view of the foregoing circumstances.

It is an object of the present invention to provide a laser generating device by an all-solid-state system for generating a laser light with a wavelength of 215 to 222 nm including a wavelength of 222 nm not affecting the human body, and having a disinfecting effect, for example, a pulse laser light with efficiency.

Solution to Problem

The present invention is as described below.

[1]

A 215- to 222-nm wavelength laser light generating device comprising:

an excitation light source part for converting a laser light with a wavelength of 1030 to 1064 nm to a second harmonic, and generating a laser light with a wavelength of 515 to 532 nm;

an optical parametric oscillating part for generating a signal light with a wavelength of 858 to 887 nm and an idler light with a wavelength of 1288 to 1330 nm using the laser light with the wavelength of 515 to 532 nm generated at the excitation light source part as an excitation light;

a separating part for separating the signal light with the wavelength of 858 to 887 nm and the idler light with the wavelength of 1288 to 1330 nm;

a first wavelength converting part for generating a fourth harmonic with a wavelength of 215 to 222 nm from the signal light with the wavelength of 858 to 887 nm;

a second wavelength converting part for generating a deep ultraviolet light with a wavelength of 215 to 222 nm by sum frequency with 258 to 266 nm of a second harmonic of the excitation light from the idler light with the wavelength of 1288 to 1330 nm; and a coupling part for coupling the fourth harmonic with the wavelength of 215 to 222 nm from the first wavelength converting part and the deep ultraviolet light with the wavelength of 215 to 222 nm from the second wavelength converting part.

[2]

The laser light generating device according to [1], of a 222-nm wavelength laser light generating device, comprising:

an excitation light source part for converting a laser light with a wavelength of 1064 nm to a second harmonic, and generating a laser light with a wavelength of 532 nm;

an optical parametric oscillating part for generating a signal light with a wavelength of 887 nm and an idler light with a wavelength of 1330 nm using the laser light with the wavelength of 532 nm generated at the excitation light source part as an excitation light;

a separating part for separating the signal light with the wavelength of 887 nm and the idler light with the wavelength of 1330 nm;

a first wavelength converting part for generating a fourth harmonic with a wavelength of 222 nm from the signal light with the wavelength of 887 nm;

a second wavelength converting part for generating a deep ultraviolet light with a wavelength of 222 nm by sum frequency with 266 nm of a second harmonic of the excitation light from the idler light with the wavelength of 1330 nm; and a coupling part for coupling the fourth harmonic with the wavelength of 222 nm from the first wavelength converting part and the deep ultraviolet light with the wavelength of 222 nm from the second wavelength converting part.

[3]

The laser light generating device according to [1] or [2], further comprising a Nd:YAG laser oscillating device for generating a laser light with a wavelength of 1030 to 1064 nm.

[4]

The laser light generating device according to any of [1] to [3], wherein the excitation light source part includes a nonlinear optical crystal for converting a laser light with a wavelength of 1030 to 1064 nm to a second harmonic.

[5]

The laser light generating device according to any of [1] to [4], wherein the optical parametric oscillating part is an optical parametric oscillating device including the nonlinear optical crystal and two mirrors.

[6]

The laser light generating device according to any of [1] to [5], wherein the first wavelength converting part includes two or more nonlinear optical crystals.

[7]

The laser light generating device according to any of [1] to [6], wherein the second wavelength converting part includes two or more nonlinear optical crystals.

[8]

The laser light generating device according to any of [1] to [7], further comprising a dichroic mirror for reflecting a light with a wavelength of 1030 to 1064 nm included in a light from the excitation light source part, and converting the light to a laser light with a wavelength of 515 to 532 nm between the excitation light source part and the optical parametric oscillating part.

[9]

The laser light generating device according to any of [1] to [8], further having a prism for separating a light with a wavelength except for a wavelength of 215 to 222 nm at a rear part of the coupling part.

[10]

The laser light generating device according to any of [1] to [9], wherein a laser light with a wavelength of 1030 to 1064 nm is a pulse laser light, and a time width of a pulse is in nanosecond or picosecond.

Advantageous Effects of Invention

The present invention produces the effect of providing a laser generating device excellent in operability capable of generating a laser light with a wavelength within the range of 215 to 222 nm including 222 nm for use in disinfection, for example, a pulse laser light with high efficiency and with ease.

By using the laser device for disinfection, it is possible to perform disinfection for a short time and effectively while avoiding the influence on the human body. For the laser light generating device in accordance with the present embodiment, necessary elements and the like are all set as solid systems, resulting in a device hardly requiring maintenance.

DESCRIPTION OF EMBODIMENTS

A 215- to 222-nm wavelength laser light generating device of the present invention includes:

- an excitation light source part for converting a laser light with a wavelength of 1030 to 1064 nm to a second harmonic, and generating a laser light with a wavelength of 515 to 532 nm;
- an optical parametric oscillating part for generating a signal light with a wavelength of 858 to 887 nm and an idler light with a wavelength of 1288 to 1330 nm using the laser light with the wavelength of 515 to 532 nm generated at the excitation light source part as an excitation light;
- a separating part for separating the signal light with the wavelength of 858 to 887 nm and the idler light with a wavelength of 1288 to 1330 nm;
- a first wavelength converting part for generating a fourth harmonic with a wavelength of 215 to 222 nm from the signal light with the wavelength of 858 to 887 nm;
- a second wavelength converting part for generating a deep ultraviolet light with a wavelength of 215 to 222 nm by sum frequency with 258 to 266 nm of a second harmonic of the excitation light from the idler light with the wavelength of 1288 to 1330 nm; and
- a coupling part for coupling the fourth harmonic with the wavelength of 215 to 222 nm from the first wavelength converting part and the deep ultraviolet light with the wavelength of 215 to 222 nm from the second wavelength converting part.

The 222-nm wavelength laser light generating device of one aspect of the laser light generating device of the present invention, includes:

- an excitation light source part for converting a laser light with a wavelength of 1064 nm to a second harmonic, and generating a laser light with a wavelength of 532 nm;
- an optical parametric oscillating part for generating a signal light with a wavelength of 887 nm and an idler light with a wavelength of 1330 nm using the laser light with the wavelength of 532 nm generated at the excitation light source part as an excitation light;
- a separating part for separating the signal light with the wavelength of 887 nm and the idler light with the wavelength of 1330 nm;
- a first wavelength converting part for generating a fourth harmonic with a wavelength of 222 nm from the signal light with the wavelength of 887 nm;
- a second wavelength converting part for generating a deep ultraviolet light with a wavelength of 222 nm by sum frequency with 266 nm of a second harmonic of the excitation light from the idler light with the wavelength of 1330 nm; and
- a coupling part for coupling the fourth harmonic with the wavelength of 222 nm from the first wavelength converting part and the deep ultraviolet light with the wavelength of 222 nm from the second wavelength converting part.

Figure 1:
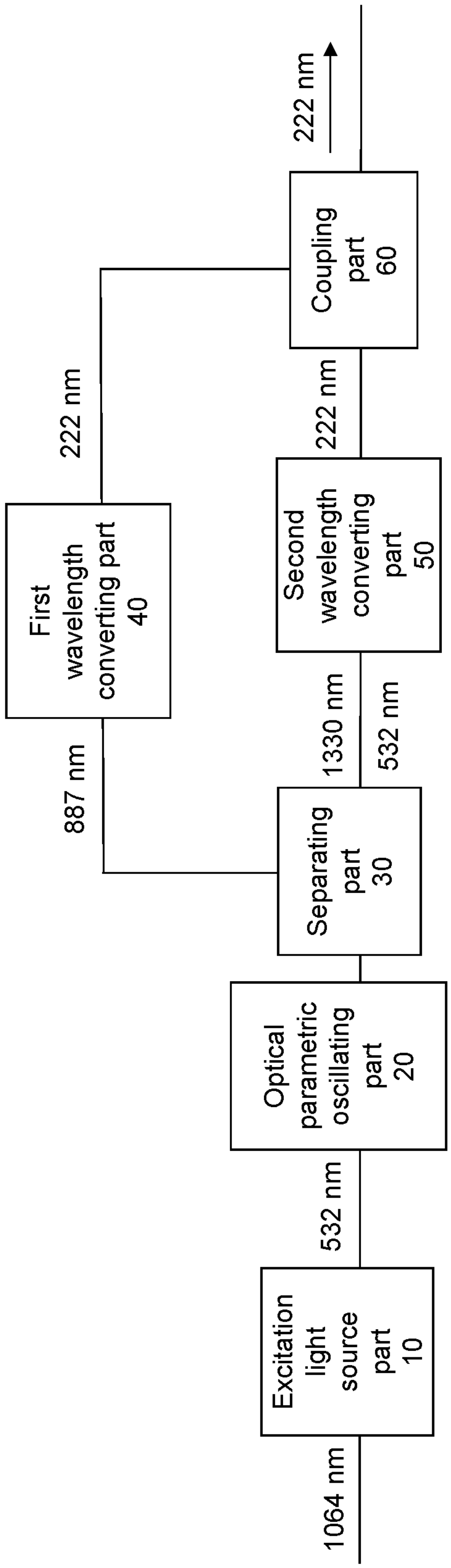
FIG. 1 is a schematic explanatory view of a laser generating device of the present invention.

A schematic explanatory view of the laser light generating device of the present invention is shown in FIG. 1 by taking a 222-nm wavelength laser light generating device as an example.

10 represents an excitation light source part, 20 represents an optical parametric oscillating part, 30 represents a separating part, 40 represents a first wavelength converting part, 50 represents a second wavelength converting part, and 60 represents a coupling part.

Figure 2:
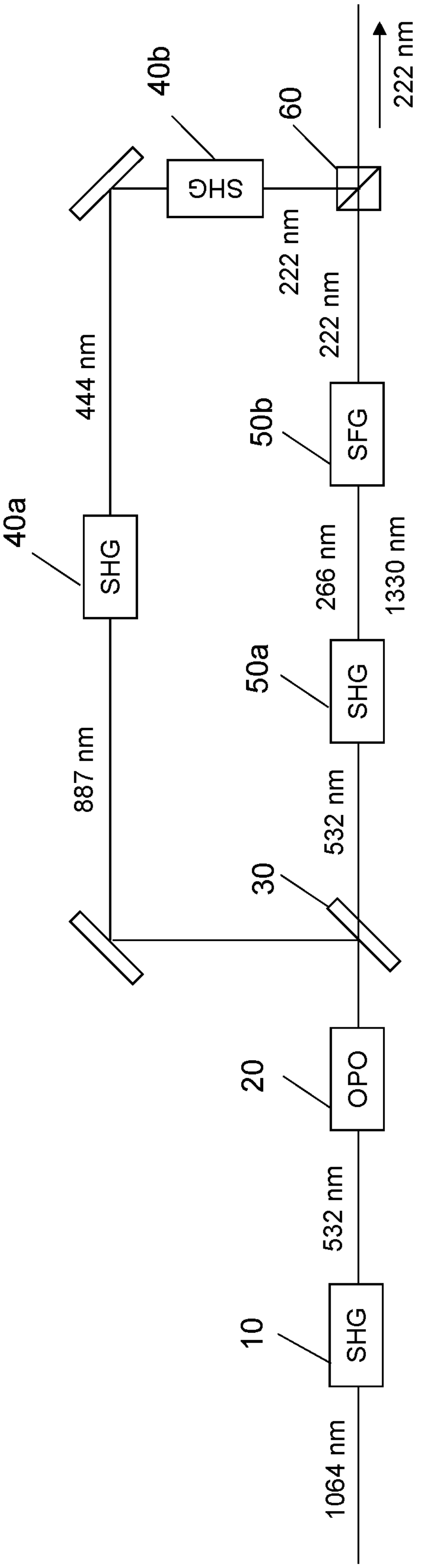
FIG. 2 shows a schematic explanatory view of one embodiment of the laser generating device of the present invention.

FIG. 2 is a schematic explanatory view of an example of a 222-nm wavelength laser light generating device as one aspect of the laser light generating device of the present invention, and particularly shows that the first wavelength converting part 40 includes a SHG **40*a* and a SHG 40*b*, and that the second wavelength converting part 50 includes a SHG 50*a* and a SFG 50*b***.

Figure 3:
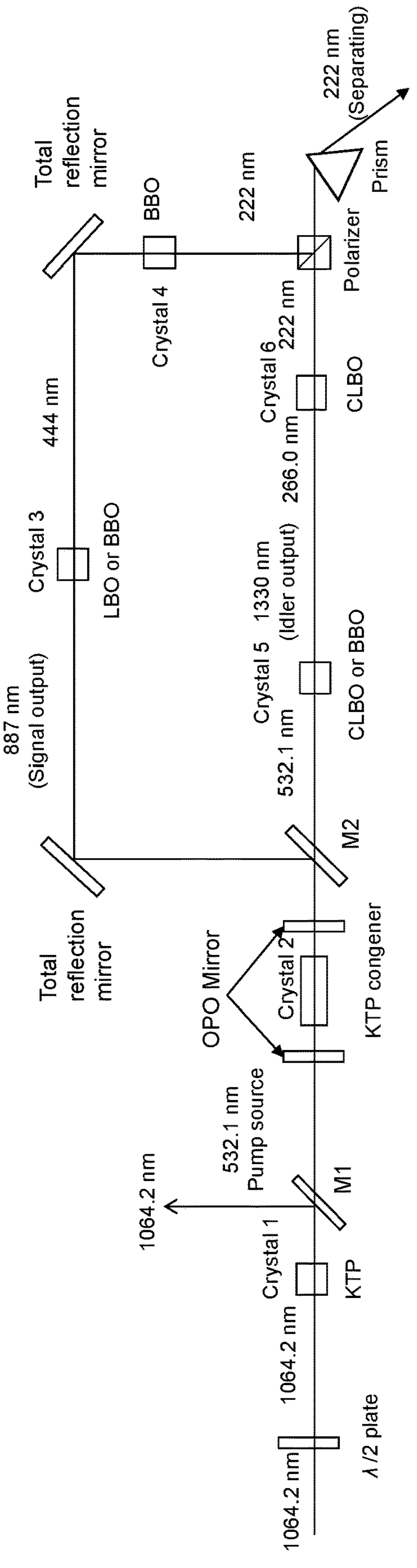
FIG. 3 shows one embodiment of the laser generating device of the present invention.

FIG. 3 shows an explanatory view of one example of a 222-nm wavelength laser light generating device of one aspect of the laser light generating device of the present invention.

The abbreviations in the DESCRIPTION of the present application mean as follows.

SHG: Second Harmonic Generation

4HG: Fourth Harmonic Generation

SFG: Sum Frequency Generation

OPO: Optical parametric oscillating part (optical parametric oscillator)

KTP: $KTiOPO_4$

BBO: $\beta$-$BaB_2O_4$

LBO: $LiB_3O_5$

RTP: $RbTiOPO_4$

KTA: $KTiOAsO_4$

MgO: PPLT: MgO-added periodically poled $LiTaO_3$

KBBF: $KBe_2BO_3F_2$

Below, the laser light generating device of the present invention will be described by taking a 222-nm wavelength laser light generating device as an example.

(Description of Excitation Light Source Part)

An excitation light source part 10 is a site for converting a laser light with a wavelength of 1064 nm into a second harmonic, and generating a laser light with a wavelength of 532 nm. The excitation light source for generating a laser light with a wavelength of 1064 nm can be, for example, a Nd:YAG ($Nd^{3+}$:$Y_3Al_5O_{12}$) laser. A 1064-nm wavelength laser light is a pulse laser light, and the time width of the pulse can be in nanosecond or picosecond. As a light source for oscillating a laser light with a wavelength of 1030 to 1064 nm, other than a Nd:YAG ($Nd^{3+}$:$Y_3Al_5O_{12}$) laser of a wavelength of 1064 nm, mention may be made of a Nd:$YVO_4$ of a wavelength of 1064 nm, Nd:YLF ($LiYF_4$) of wavelengths of 1053 nm and 1047 nm, Yb:YAG of a wavelength of 1030 nm, Nd:$GdVO_4$ of a wavelength 1063 nm, or the like. For the wavelength conversion of the laser light source, the secondary nonlinear optical effect is used. For this reason, basically, a pulse light source for generating a strong electric field is used. However, use of a resonator in combination in each process also enables wavelength conversion of a continuous light.

The excitation light source part 10 can include, for example, an excitation light source, and a nonlinear optical crystal for converting the laser light to a 532-nm laser light of a second harmonic. The nonlinear optical crystal can be, for example, a KTP crystal, and is indicated with a crystal 1 in FIG. 3. The crystal 1 can also be any of, for example, BBO, LBO, MgO:PPLT, and PPKTP other than the KTP crystal. PP of "PP+crystal name" is the abbreviation of "Periodically Poled".

More specifically, when the KTP crystal is used as the nonlinear optical crystal, as shown in FIG. 3, a laser light from the excitation light source is passed through a half-wave plate (λ/2 plate) so that the polarization direction was set at 45 degrees diagonally. Then, the laser light is passed though the crystal 1, thereby to be converted to a 532-nm laser light of a second harmonic. The phase matching in wavelength conversion is of the type 2. Whereas, when an LBO or BBO crystal is used for the crystal 1, the polarization direction is made the direction perpendicular to the paper plane though a λ/2 plate. Then, the laser light is passed through the crystal 1, thereby to be converted to a 532-nm laser light of a second harmonic. Further, when MgO:PPLT or PPKTP is used for the crystal 1, a λ/2 is not necessary. The crystal 1 is set so that the polarization direction of the 532-nm laser light may become the direction in parallel with the paper plane. The phase matching of the type 2 means phase matching for generating a secondary harmonic from an incident lights of different light beams (i.e., different polarized lights orthogonal to each other), and is distinguished from phase matching of the type 1 of generating a secondary harmonic of a different polarized light from the incident light from the incident light of the same light beam (i.e., the same polarized light). Further, the phase matching resulting in that all of the incident light and the second harmonic are in the direction of the same extraordinary ray is referred to as type 0 in the present description.

A list of the kind and the functions, the type of phase matching, and polarization of the crystal usable in the excitation light source part, the optical parametric oscillating part, the first wavelength converting part, and the second wavelength converting part is shown in Table 1. Table 1 shows the case of the light source wavelength of 1064 nm as an example. When the crystal usable described for each of crystals 1 to 6 has a light source wavelength within the range of 1030 to 1064 nm, it has the function, the phase matching type, and polarization shown in Table 1.

TABLE 1

| Wavelength converting part | Crystal | Function | Type of phase matching | Polarization | Usable crystal |
|---|---|---|---|---|---|
| Excitation light part | Crystal 1 | SHG 1064 nm → 532 nm | Type 0 | e + e → e | PPLT, PPKTP |
| | | | Type 1 | o + o → e | BBO, LBO |
| | | | Type 2 | e + o → e | KTP |
| Optical parametric oscillating part | Crystal 2 | OPO 532 nm → 1330 nm + 887 nm | Type 0 | e → e + e | PPLT, PPKTP |
| | | | Type 1 | e → o + o | BBO |
| | | | Type 2 | o → o + e | KTP, RTP, KTA, BBO |
| First wavelength converting part | Crystal 3 | SHG 887 nm → 444 nm | Type 0 | e + e → e | MgO:PPLT, PPKTP |
| | | | Type 1 | o + o → e | BBO, LBO |
| | Crystal 4 | SHG 444 nm → 222 nm | Type 1 | o + o → e | BBO, KBBF |
| Second wavelength converting part | crystal 5 | SHG 532 nm → 266 nm | Type 1 | o + o → e | BBO, CLBO |
| | crystal 6 | SFG 1330 nm + 266 nm → 222 nm | Type 1 | o + o → e | BBO, CLBO |
| | | | Type 2 | e + o → e | BBO, CLBO |

"o" in the column of polarization in Table 1 means an ordinary wave, and "e" means an extraordinary wave.

(Dichroic Mirror M1)

A dichroic mirror (M1 in FIG. 3) can be provided between the excitation light source part 10 and the OPO 0. The dichroic mirror M1 can reflect a 1064-nm light included in the light from the excitation light source part 10, and can make a 532-nm laser light. A 1064-nm light is nor used in the subsequent processes, and hence is separated from a 532-nm laser light. This can avoid the following: when laser with other wavelengths is condensed in subsequent processes, the optical elements are applied with unnecessary damages, and a temperature load is applied to the crystal. A 532-nm laser light transmitted through the dichroic mirror M1 is made incident upon the OPO.

(Description of Optical Parametric Oscillating Part (OPO))

The OPO 20 is a site for generating a signal light with a wavelength of 887 nm and an idler light with a wavelength of 1330 nm with a laser light with a wavelength of 532 nm generated at the excitation light source part as an excitation light, and separating the generated signal light. The OPO includes a nonlinear optical crystal and two mirrors. The nonlinear optical crystal can be, for example, a KTP crystal or a congener crystal thereof, and is indicated with a crystal 2 in FIG. 3. As the congener crystal of a KTP crystal, for example, mention may be made of a RTP, or KTA crystal, and other than these, mention may be made of any of BBO, MgO:PPLT, or PPKTP. The crystal 2 is cut to a phase matching angle for generating a signal light λs with a wavelength of 887 nm and an idler light λi with a wavelength of 1330 nm. MgO:PPLT and PPKTP are adjusted so as to have a polarization reversal period length capable of generating the signal light and idler light wavelengths. The two wavelengths generated from the crystal is amplified by a resonator including two mirrors, resulting in OPO oscillation. When the crystal 2 constituting the optical parametric oscillating part 20 is set as the congener crystal of a KTP crystal, phase matching is the process of type 2. For this reason, the excitation light and the idler light are polarized lights horizontal with the paper plane, and the signal light is polarized in the direction perpendicular to the paper plane. When the crystal 2 constituting the optical parametric oscillating part 20 is set as a BBO crystal to provide type-1 phase matching, assuming that the excitation light is a polarized light horizontal with the paper plane, the signal light and the idler light are polarized in the direction perpendicular to the paper plane. When the crystal 2 constituting the optical parametric oscillating part 20 is set as a MgO:PPLT or PPKTP crystal, phase matching is the process of type 0. For this reason, the excitation light, the signal light, and the idler light are polarized in the direction horizontal with the paper plane.

(Separating Part 30)

A separating part 30 for separating a signal light with a wavelength of 887 nm and an idler light with a wavelength of 1330 nm is provided between the OPO and the first wavelength converting part and the second wavelength converting part. The separating part 30 preferably transmits a 1330-nm idler light and a 532-nm excitation light which has not been converted in consideration of the subsequent processes. The separating part 30 can be, for example, a dichroic mirror (M2 in FIG. 3). At the dichroic mirror M2, of the signal light and the idler light converted at the OPO, only an 887-nm signal light is reflected, and a 1330-nm idler light, and a 532-nm excitation light which has not been converted are transmitted. When the polarization directions of the signal light and the idler light are different (type-2 phase matching), a polarizer can be used as the separating part 30. In this case, a horizontally polarized light is transmitted through the polarizer, and a perpendicularly polarized light is reflected.

(First Wavelength Converting Part 40)

The first wavelength converting part 40 is a 4-HG site from a signal light with a wavelength of 887 nm to a wavelength of 222 nm, and specifically, as shown in FIG. 2, can include a SHG 40*a* for converting a 887-nm signal light to a 444-nm blue light and a SHG 40*b* for converting a 444-nm light to a 222-nm deep ultraviolet light.

The SHG 40*a* converts a reflected 887-nm signal light to a 444-nm blue light when the separating part 30 is a dichroic mirror M2. The SHG 40*a* can be, for example, a nonlinear optical crystal such as an LBO or BBO crystal, and is indicated with a crystal 3 in FIG. 3. The crystal 3 is cut to an angle for subjecting a basic wave with a wavelength of 887 nm to type-1 phase matching to a SHG with a wavelength of 444 nm. The polarization direction of a 444-nm light is a horizontal direction. When the crystal 2 constituting the optical parametric oscillating part 20 is set as a MgO:PPLT or a PPKTP crystal, the SHG 40*a* is set as a MgO:PPLT crystal having a polarization reversal period length for generating an 888-nm SHG. Also in this case, the polarization direction of a 444-nm light is the horizontal direction.

The SHG 40*b* convers a 444-nm light to a 222-nm deep ultraviolet light, and can be, for example, a nonlinear optical crystal such as a BBO. In FIG. 3, the SHG 40*b* is indicated with a crystal 4. A 444-nm light is made incident upon the BBO of the crystal 4, and is further converted to a SHG, resulting in a deep ultraviolet light with a wavelength of 222 nm. The crystal 4 can be, for example, a nonlinear optical crystal such as a KBBF other than the BBO, and is cut or inserted in a quartz prism so that the basic wave may propagate at an angle for subjecting the basic wave with a wavelength of 444 nm to type-1 phase matching to a SHG with a wavelength of 222 nm. The polarization direction of a 222-nm light is the direction perpendicular to the paper plane. The generated 222 nm is synthesized with the 222-nm light generated on another side at a coupling part 60.

The first wavelength converting part 40 can include two or more crystals. When the SHG 40*a* and the SHG 40*b* each include one crystal, the first wavelength converting part 40 includes two crystals. The SHG 40*a* and the SHG 40*b* can each be an object including two crystals respectively having the same length and cut angle arranged in tandem. This can increase the conversion efficiency. In that case, the first wavelength converting part 40 can include three or more crystals.

(Second Wavelength Converting Part 50)

The second wavelength converting part 50 is a site for generating a deep ultraviolet light with a wavelength of 222 nm by sum frequency with 266 nm of the second harmonic of an excitation light from the idler light with a wavelength of 1330 nm separated at the separating part 30. As shown in FIG. 2, the second wavelength converting part includes a SHG 50*a* for converting an excitation light with a wavelength of 532 nm to a wavelength of 266 nm, and a SFG 50*b* for making the deep ultraviolet light with a wavelength of 266 nm and the idler light with a wavelength of 1330 nm generated from the OPO incident thereupon again, and generating 222 nm by sum frequency mixing.

The SHG 50*a* can be a nonlinear optical crystal of, for example, BBO or CLBO, and is indicated with a crystal 5 in FIG. 3. Of the excitation light and the idler light which have passed through the dichroic mirror M2 of the separating part 30, the excitation light with a wavelength of 532 nm is made incident upon the crystal 5, and is converted to a wavelength of 266 nm by SHG. The crystal 5 is cut to an angle for subjecting the basic wave with a wavelength of 532 nm to type-1 phase matching to a SHG with a wavelength of 266 nm. The polarization direction of a 266-nm light at this step is the perpendicular direction.

For the SFG 50*b*, the nonlinear optical crystal of, for example, a CLBO crystal can be used, and is indicated with a crystal 6 in FIG. 3. The deep ultraviolet light with a wavelength 266 nm converted with the crystal 5, and the idler light with a wavelength of 1330 nm generated from the OPO are made incident upon the crystal 6 again, thereby generating 222 nm by sum frequency mixture. The crystal 6 can be the nonlinear optical crystal of, for example BBO other than the CLBO, and the crystal 6 is cut so as to provide type-2 phase matching. The polarization direction of the generated 222-nm light is the horizontal direction. When the crystal 2 constituting the optical parametric oscillating part 20 is set as a BBO for type-1 phase matching, the crystal 6 is cut so as to provide type-1 phase matching.

The second wavelength converting part 50 can include two or more crystals. When the SHG 50*a* and the SFG 50*b* each include one crystal, the second wavelength converting part 50 includes two crystals. The SHG 50*a* and the SFG 50*b* can each be an object including two crystals respectively having the same length and cut angle arranged in tandem. This can increase the conversion efficiency. In that case, the second wavelength converting part 50 can include three or more crystals.

(Coupling Part 60)

The coupling part 60 synthesizes the 222-nm light generated at the first wavelength converting part 40 (the SHG 40*b* in FIG. 2), and the 222-nm light generated at the second wavelength converting part 50 (the SFG 50*b* in Fig.). The coupling part 60 can be, for example, a polarizer.

The rear part of the coupling part 60 can be provided with a separating part 70 (not shown in FIGS. 1 and 2) for separating the laser lights with various wavelengths generated during the process of wavelength conversion, and extracting a 222-nm light. The separating part 70 can be, for example, a prism (see FIG. 3). The prism has no particular restriction so long as it can remove laser lights with wavelengths other than 222 nm generated in the process of wavelength conversion, and can be, for example, a quartz prism or a $MgF_2$ prism. At the separating part 70, lights with wavelengths other than 222 nm are separated, resulting in a laser light with a wavelength of 222 nm.

The example shown in FIG. 3 is the case where the optical parametric oscillating part is of the type 2. The examples of combinations of crystals 2 to 6 in the case of the type 0 and in the case of the type 1 are shown in Table 2 below together with the case of the type 2 shown in FIG. 3. However, the examples are merely illustrative, and it is not intended that the present invention is limited to the examples. The examples of combinations of the crystals 2 to 6 shown in Table 2 are the examples when the light source wavelength is 1064 nm. When the light source wavelength falls within the range of 1030 to 1064 nm, the same combinations as those of the crystals 2 to 6 shown in Table 2 can be adopted.

TABLE 2

| Type of phase matching of optical parametric oscillating part crystal | | Crystal 2 | Crystal 3 | Crystal 4 | Crystal 5 | Crystal 6 |
|---|---|---|---|---|---|---|
| Optical parametric oscillating part | Case of type 0 | MgO:PPLT or PPKTP | MgO:PPLT | BBO or KBBF | CLBO or BBO | CLBO or BBO (Either is Type-2) |
| | Case of type 1 | BBO | LBO or BBO | BBO or KBBF | CLBO or BBO | CLBO or BBO (Either is Type-1) |
| | Case of type 2 | KTP congener or BBO | LBO or BBO | BBO or KBBF | CLBO or BBO | CLBO or BBO (Either is Type-2) |

(Generation Mechanism of Laser Light with a Wavelength 215 to 222 nm)

The mechanism for generating a laser light with a wavelength of 215 to 222 nm in the device of the present invention will be described below by taking 222 nm as an example.

In the case of an excitation light wavelength of λp, a signal light wavelength of λs, and an idler light wavelength of λi at the optical parametric oscillator (OPO), the following relationship holds.

$$1/\lambda s+1/\lambda i=1/\lambda p \quad \text{(Math. 1)}$$

Further, the SFG has the following relationship in the case of an incident light wavelength of λi, another incident light wavelength of λ2, and a sum frequency generation wavelength of λ3.

$$1/\lambda i+1/\lambda 2=1/\lambda 3 \quad \text{(Math. 2)}$$

In the ultraviolet ray laser generating system by wavelength conversion, there are various combinations using (Math. 1) and (Math. 2). The foregoing relationship generates a coherent light with a desirable wavelength. Normally, by using the output light of any one of the signal light or the idler light of (Math. 1) for wavelength conversion, a deep ultraviolet laser light has been generated. The other output light has not been used, and has been cut by a filter. This has undesirably resulted in a defect of a low conversion efficiency to a deep ultraviolet of the overall system.

Figure 4:
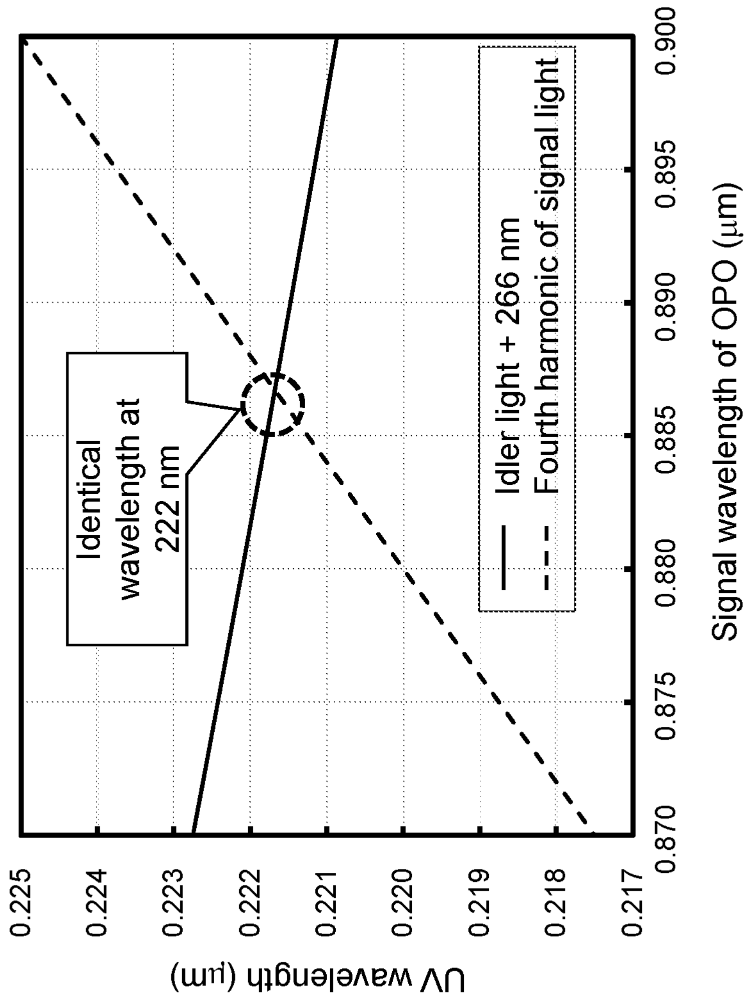
FIG. 4 shows an explanatory view illustrating that the wavelength of the fourth harmonic of the signal light λs of the OPO, and the wavelength of the sum frequency generation of the idler light λi of the OPO with a 266-nm light of the second harmonic of a 532-nm light of the excitation light are in agreement with each other at 222 nm.

In the present invention, as described above, at the OPO of excitation with 532 nm of the second harmonic of a 1064-nm laser light, an 887-nm signal light λs and an idler light λi with a wavelength of 1330 nm are generated. There is used the characteristic that the wavelength of 222 nm of the fourth harmonic generated from the 887-nm signal light λs at the first wavelength converting part, and the wavelength of the sum frequency generation generated from the idler light λi with a wavelength of 1330 nm and the 266-nm light of the second harmonic of the 532-nm light of the excitation light at the succeeding second wavelength converting part are in agreement with each other at 222 nm as shown in FIG. 4. The mechanism similarly functions when using a laser light light source with a wavelength within the range of 1030 to 1064 nm, a deep ultraviolet light with a wavelength within the range of 215 to 222 nm is generated.

In the present invention, it becomes possible to use the output lights of both the signal light and the idler light of the OPO for generation of a deep ultraviolet light with a wavelength of 215 to 222 nm. For this reason, a more efficient 215- to 222-nm wavelength deep ultraviolet laser light generating device can be implemented.

Although a laser light with a wavelength of 222 nm generated by the device of the present invention may fluctuate according to the specifications and the operation conditions of respective members, the light is a laser light with a wavelength within the range of roughly 221.5 to 222.1 nm. The laser light with a wavelength other than a wavelength of 222 nm similarly has a wavelength falling within the range of roughly±0.5 nm or less according to the specifications and the operation conditions of respective members.

The laser light with a wavelength of 222 nm obtained with the device of the present invention is only a deep ultraviolet ray with a wavelength of 222 nm contributing to the disinfecting effect. Accordingly, as distinct from the case where a KrCl lamp tube with a broad spectrum is used as the light source, a band pass filter for cutting the extra deep ultraviolet ray affecting the human body is unnecessary.

The laser light generating device of the present invention enables a relatively higher output power, and hence enables application of a deep ultraviolet ray with a wavelength of 222 nm to a wide region, and application to a liquid such as water, and is available for uses of disinfection of the gateway of a facility where unspecified people enter and exit, and a liquid, and the like. Additionally, the generated laser light can be applied to the object via a laser light conductor such as a fiber, if required. Therefore, for example, application of ultraviolet rays to the portion such as the rear side of a structure becomes easy.

INDUSTRIAL APPLICABILITY

The present invention is effective certainly in the medical scene, and also in disinfection work in a large scale facility. Further, a toxic gas such as ethylene oxide including ozone is not used because of less effect on the human body, and hence the effect on the human body is less and handling is easy. Furthermore, a liquid for alcohol disinfection or the like is not used, and hence the present invention is usable for disinfection of the paper media not to be wetted with water such as books.

REFERENCE SIGNS LIST

10 Excitation light source part
20 Optical parametric oscillating part
30 Separating part
40 First wavelength converting part

50 Second wavelength converting part
60 Coupling part

The invention claimed is:

1. A 215- to 222-nm wavelength laser light generating device comprising:

an excitation light source part for converting a laser light with a wavelength of 1030 to 1064 nm to a second harmonic and for generating a laser light with a wavelength of 515 to 532 nm;

an optical parametric oscillating part for generating a signal light with a wavelength of 858 to 887 nm and an idler light with a wavelength of 1288 to 1330 nm using the laser light with the wavelength of 515 to 532 nm generated at the excitation light source part as an excitation light;

a separating part for separating the signal light with the wavelength of 858 to 887 nm and the idler light with the wavelength of 1288 to 1330 nm;

a first wavelength converting part for generating a fourth harmonic with a wavelength of 215 to 222 nm from the signal light with the wavelength of 858 to 887 nm;

a second wavelength converting part for generating a deep ultraviolet light with a wavelength of 215 to 222 nm by sum frequency with 258 to 266 nm of a second harmonic of the excitation light from the idler light with the wavelength of 1288 to 1330 nm; and a coupling part for coupling the fourth harmonic with the wavelength of 215 to 222 nm from the first wavelength converting part and the deep ultraviolet light with the wavelength of 215 to 222 nm from the second wavelength converting part.

2. The laser light generating device according to claim 1, further comprising a Nd: YAG laser oscillating device for generating the laser light with a wavelength of 1030 to 1064 nm.

3. The laser light generating device according to claim 1, wherein the excitation light source part includes a nonlinear optical crystal for converting the laser light with a wavelength of 1030 to 1064 nm to a second harmonic.

4. The laser light generating device according to claim 1, wherein the optical parametric oscillating part is an optical parametric oscillating device including a nonlinear optical crystal and two mirrors.

5. The laser light generating device according to claim 1, wherein the first wavelength converting part includes two or more nonlinear optical crystals.

6. The laser light generating device according to claim 1, wherein the second wavelength converting part includes two or more nonlinear optical crystals.

7. The laser light generating device according to claim 1, further comprising:

a dichroic mirror for reflecting the light with a wavelength of 1030 to 1064 nm included in a light from the excitation light source part and for converting the light to the laser light with a wavelength of 515 to 532 nm between the excitation light source part and the optical parametric oscillating part.

8. The laser light generating device according to claim 1, further comprising a prism for separating a light with a wavelength except for a wavelength of 215 to 222 nm at a rear part of the coupling part.

9. The laser light generating device according to claim 1, wherein the laser light with a wavelength of 1030 to 1064 nm is a pulse laser light, and a time width of a pulse is in nanosecond or picosecond.

10. A 222-nm wavelength laser light generating device, comprising:

an excitation light source part for converting a laser light with a wavelength of 1064 nm to a second harmonic and for generating a laser light with a wavelength of 532 nm;

an optical parametric oscillating part for generating a signal light with a wavelength of 887 nm and an idler light with a wavelength of 1330 nm using the laser light with the wavelength of 532 nm generated at the excitation light source part as an excitation light;

a separating part for separating the signal light with the wavelength of 887 nm and the idler light with the wavelength of 1330 nm;

a first wavelength converting part for generating a fourth harmonic with a wavelength of 222 nm from the signal light with the wavelength of 887 nm;

a second wavelength converting part for generating a deep ultraviolet light with a wavelength of 222 nm by sum frequency with 266 nm of a second harmonic of the excitation light from the idler light with the wavelength of 1330 nm; and a coupling part for coupling the fourth harmonic with the wavelength of 222 nm from the first wavelength converting part and the deep ultraviolet light with the wavelength of 222 nm from the second wavelength converting part.

* * * * *